United States Patent [19]

Moake et al.

[11] Patent Number: 4,704,580
[45] Date of Patent: Nov. 3, 1987

[54] METHOD AND APPARATUS FOR MEASURING THE DEPTH OF LOCAL DEFECTS IN FERROMAGNETIC ELEMENTS

[75] Inventors: Gordon L. Moake; James E. Bradfield, both of Houston, Tex.

[73] Assignee: PA Incorporated, Houston, Tex.

[21] Appl. No.: 599,228

[22] Filed: Apr. 11, 1984

[51] Int. Cl.⁴ .................. G01N 27/82; G01N 27/72; G01R 33/12

[52] U.S. Cl. .................. 324/242; 324/227; 324/232

[58] Field of Search ............... 324/228, 225, 226, 227, 324/232, 239, 240, 242, 243

[56] References Cited

U.S. PATENT DOCUMENTS

| | | | |
|---|---|---|---|
| 2,467,306 | 4/1949 | Habig | 324/242 |
| 2,527,000 | 4/1983 | Drake | 324/232 |
| 2,560,845 | 2/1971 | Goldberg et al. | 324/243 |
| 2,882,488 | 4/1959 | Price et al. | 324/225 |
| 2,886,772 | 5/1959 | Gresham et al. | 324/241 |
| 3,103,976 | 9/1963 | de Vries et al. | 324/207 |
| 3,197,693 | 7/1965 | Libby | 324/225 |
| 3,237,446 | 3/1966 | Wood | 324/226 |
| 3,328,681 | 6/1967 | Wood | 324/225 |
| 3,337,796 | 8/1967 | Hentschel et al. | 324/233 |
| 3,343,079 | 9/1967 | Crouch | 324/227 |
| 3,379,970 | 4/1968 | Kusenberger et al. | 324/227 |
| 3,401,332 | 9/1968 | McClurg et al. | 324/227 |
| 3,529,236 | 9/1970 | Proctor | 324/260 |
| 3,538,433 | 11/1970 | Wood et al. | 324/227 |
| 3,555,412 | 1/1971 | Fowler | 324/228 |
| 3,579,099 | 5/1971 | Kanbayashi | 324/235 |
| 3,609,530 | 9/1971 | Johnson | 324/225 |
| 3,612,987 | 10/1971 | Packe et al. | 324/242 |
| 3,693,075 | 9/1972 | Forster | 324/229 |
| 3,835,374 | 9/1974 | Frost | 324/220 |
| 3,843,923 | 10/1974 | de Vries et al. | 324/228 |
| 3,916,301 | 10/1975 | Vild et al. | 324/226 |
| 3,940,689 | 2/1976 | Johnson, Jr. | 324/221 |
| 4,061,967 | 12/1977 | Hall | 324/260 |
| 4,079,310 | 3/1978 | Osborne et al. | 324/226 |
| 4,096,437 | 6/1978 | Kitzinger et al. | 324/227 |
| 4,101,832 | 7/1978 | Baker et al. | 324/227 |
| 4,247,819 | 1/1981 | Shimanda et al. | 324/233 |
| 4,270,088 | 5/1981 | Weischedel | 324/241 |
| 4,292,588 | 9/1981 | Smith | 324/221 |
| 4,292,589 | 9/1981 | Bonner | 324/221 |
| 4,379,261 | 7/1978 | Lakin | 324/227 |
| 4,485,344 | 11/1984 | de Sivry et al. | 324/207 |
| 4,538,108 | 8/1985 | Huschelrath et al. | 324/232 |
| 4,611,170 | 9/1986 | Stanley et al. | 324/229 |

FOREIGN PATENT DOCUMENTS 913780 12/1962 United Kingdom .

Primary Examiner—Reinhard J. Eisenzopf
Assistant Examiner—Walter E. Snow
Attorney, Agent, or Firm—Norvell & Associates

[57] ABSTRACT

A method and apparatus for determining the extent of defects in ferrogmagnetic elements, such as tubing comprising a continuous string for use in an oil or gas well is disclosed. The tubing trip tool measures the depth of local defects, such as corrosion pitting, during removal of the tubing from the well. Tubing velocity is also measured, and couplings between tubing sections are detected and counted, in order to specify the axial location of defects on each tube, and also provide a profile of the condition of the overall string. A saturating magnetic field is applied to the tubing and a comparison of two derivatives of flux leakage is made to quantify defects in the tubing.

31 Claims, 13 Drawing Figures

METHOD AND APPARATUS FOR MEASURING THE DEPTH OF LOCAL DEFECTS IN FERROMAGNETIC ELEMENTS

BACKGROUND OF THE INVENTION

1. Field of the Invention

This invention relates to defect inspection of tubular elements comprising a generally continuous tubular string used in a subterranean oil and gas well, and more particularly to inspection of tubular elements by detecting the properties of magnetic fields induced in the tubular elements during removal from the well.

2. Description of the Prior Art

Continuous tubular strings formed of connectable tubular sections or elements, such as production tubing strings, strings of drill pipe and casing strings, are used in the drilling, completion and production of subterranean oil and gas wells. The tubular elements comprising such strings are subject to mechanical damage while the tubular elements are located within the well and are also subject to the action of corrosive fluids which may be contained within the tubular elements or which may be transported through the tubular string between the well surface and a downhole location. It is therefore advantageous that the individual tubular elements comprising a tubular string be inspected periodically. Commonly, tubular elements or tubular sections are inspected for defects after the tubing string is removed from the well. Conventional inspection of tubular sections normally occurs after the individual tubing sections comprising the tubing string have been disengaged. Defect inspections are conventionally performed on a section by section basis. Occasionally, inspection is performed downhole through the use of inspection calipers. These tools leave "caliper tracks" and can be affected by the contents of the tubing.

A number of techniques exist for determining the presence of a defect in a tubing section. For example, the precise location of internal and external radially extending and three dimensional defects, including slug inclusions, mechanical damage, corrosion pitting and fatigue cracks has been determined by flux leakage techniques in which a longitudinal magnetic field is induced by one or more magnetic induction coils. Surface riding detectors are located around the tubing and the maximum signal is recorded to precisely locate the defect. Since this magnetic inspection is conducted on a section by section basis after disengagement from the tubing string, when surface dirt, scale and mud can be controlled, detectors can be placed directly on the surface of the ferromagnetic tubular section to determine the presence of defects.

The location of longitudinal defects, including internal and external seams, plug scores, eccentricity, wear due to sucker rod interference, and wireline cuts, has been detected by inducing a circumferential magnetic field in the tubing. The field is induced by a high current discharge through an insulated rod on the interior of the tubing section. Detectors rotating around the surface of the tubing locate these longitudinal defects. Again, since the inspection is conducted on a section by section basis, the insulated rod can be inserted through the interior of the tubing section for this longitudinal defect inspection technique.

Other conventional inspection systems use methods which do not require insertion of rods and probes inside the pipe. Specifically, a common way of detecting longitudinal defects magnetically is the "rotating pole" method, where the magnetic field is applied from the outside by rotating electromagnets, and detectors positioned in-between the poles scan the outside surface of the pipe.

Tubing wall thickness has been measured by measuring the radiation from a rotating radioactive source of gamma radiation transmitted through the wall of a tubing section. For example, with a source rotating around the pipe a detector may be located on the inside of the pipe to determine the degree of attenuation of gamma radiation and thus to determine the wall thickness. Again, this technique requires access to individual tubing sections after disengagement of the string. Other ways of measuring wall thickness with gamma radiation, which are backscatter, double-wall through-transmission and chord, have both the radiation detector and the source located on the outside of the pipe. Radiation methods introduce such problems as radiation licensing, record keeping, radiation safety administration, source handling complications, and fear of the unknown.

Techniques requiring surface-riding detectors, insertion of a detector or a driving means within the bore of tubular elements or requiring rotating mechanical means to obtain a complete circumferential coverage of tubing sections are unsuited for use in defect inspection and measurement of tubing sections while the string is being removed from the well. These defect inspection techniques are also unsuited to the measurement of defects in tubing sections while the sections are interconnected in the tubing string. Thus these inspection techniques are not suitable for use on a drilling, completion or workover rig at the surface of the well to measure defects in a tubing string as the string is removed from the well. In addition to the requirements that only disengaged tubing sections be individually measured, additional problems which would be encountered are the limited space available on the rig, the inability to control the longitudinal velocity of the tubing string as it is removed from the well, and the difficulty in precisely controlling the transverse location of the tubing sections comprising the tubing string. Furthermore, the use of surface detectors in a tubing trip tool for measuring defects as tubing sections, comprising a tubing string, are removed from the well is also complicated by the presence of solid deposits, such as drilling mud, and tubing mounted components, such as retrievable packers, which may be incorporated into the tubing string.

One technique for inspecting tubular elements which is adaptable to relative movement, at variable velocities, is a technique involving the use of a saturating longitudinal magnetic field and the subsequent measurement of the time integral of the electrical signal caused by the magnetic field applied to the ferromagnetic tubular member to determine the average wall thickness. Testing using this technique has been conducted for surface pipe installations in which the magnetic field and the flux detecting elements are moved relative to a continuous pipe array. Such apparatus has not, however, been employed to measure the average wall thickness of tubing sections as they are removed from an oil or gas well.

SUMMARY OF THE INVENTION

The method and apparatus disclosed herein is used to determine the extent of defects in ferromagnetic tubular elements comprising a continuous string used in an oil or gas well. The tubing trip tool measures tubing average wall thickness, local defects, such as corrosion pitting, and longer axial defects during removal of the tubing from the well.

A uniform magnetic property is induced in at least a portion of the tubing. In the preferred embodiment, an appropriate longitudinal magnetic field is induced by applying an appropriate uniform magnetizing field. The magnitude of the electric signal integral from this field determines the tubing wall thickness.

Flux leakage in the longitudinal magnetic field is related to the presence of local defects, such as corrosion pitting. the shape of the flux leakage field is determined, for example by geometric signal processing, to quantify the depth of the local defects. In the preferred embodiment, multiple flux leakage detecting elements, such as Hall effect probes, are used to determine two different derivatives of the flux leakage, and the depth of the local defects, such as corrosion pits, is a function of both different derivatives evaluated at their local maximums.

The presence of axial defects, having an axial dimension in excess of the local defects, is determined by applying a fluctuating magnetic field in addition to the first uniform magnetic field. Driven fields induced in the tubing element by the fluctuating field are then used to measure the axial defects. In the preferred embodiment the fluctuating fields are generated by two coils having sinusoidal distributions of different phases around the tubing. The driven fields are also detected by using two sinusoidal detector coils having sinusoidal conductor distributions of different phases. The applied fluctuating field is rotated around the tubing using stationary coils and the presence of axially extending defects at various angular positions can be detected.

DESCRIPTION OF THE PREFERRED EMBODIMENTS

TUBING TRIP TOOL

Figure 1:
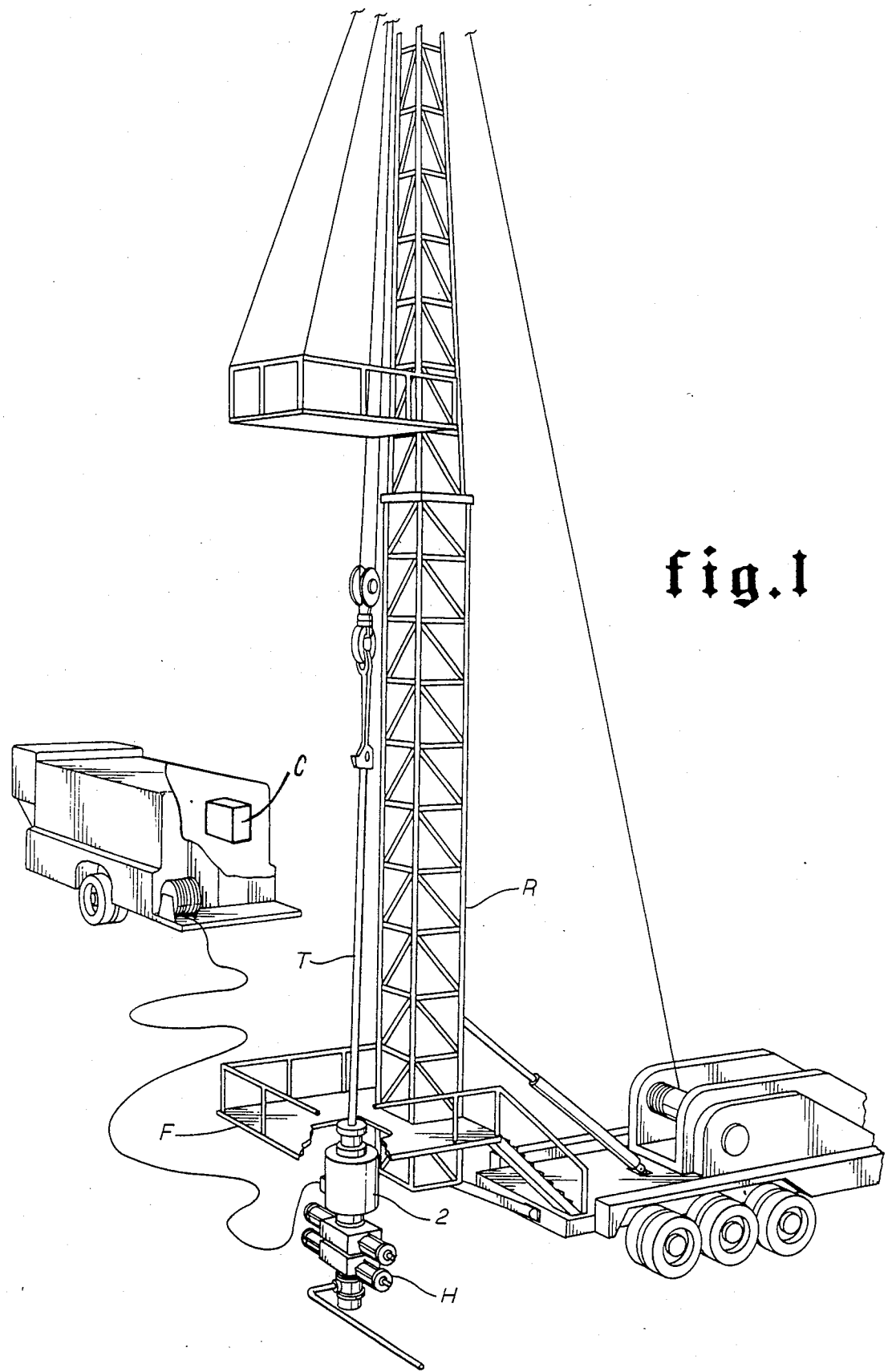
FIG. 1 is a schematic showing a tubing trip tool on a surface rig.

A conventional workover rig illustrated schematically by rig R in FIG. 1, is used to remove a tubular string, such as a casing, drilling or tubing string represented by tubing string T, from an oil or gas well during workover operations. Workover operations normally involve the removal of the tubular string to permit operations intended to restore or increase production in a producing well. Typically the original tubing string is reused if the respective tubular elements are in satisfactory condition. FIG. 1 illustrates the use of a tubing trip tool 2 at the rig site to measure defects in each tubular element as it is removed from the well. A tubing trip tool 2 comprising the preferred embodiment of this invention can be positioned on the wellhead H below the rig floor F so as not to interfere with conventional operations on the rig. The tubing trip tool can be attached directly to the blow out preventers on the well.

Figure 2:
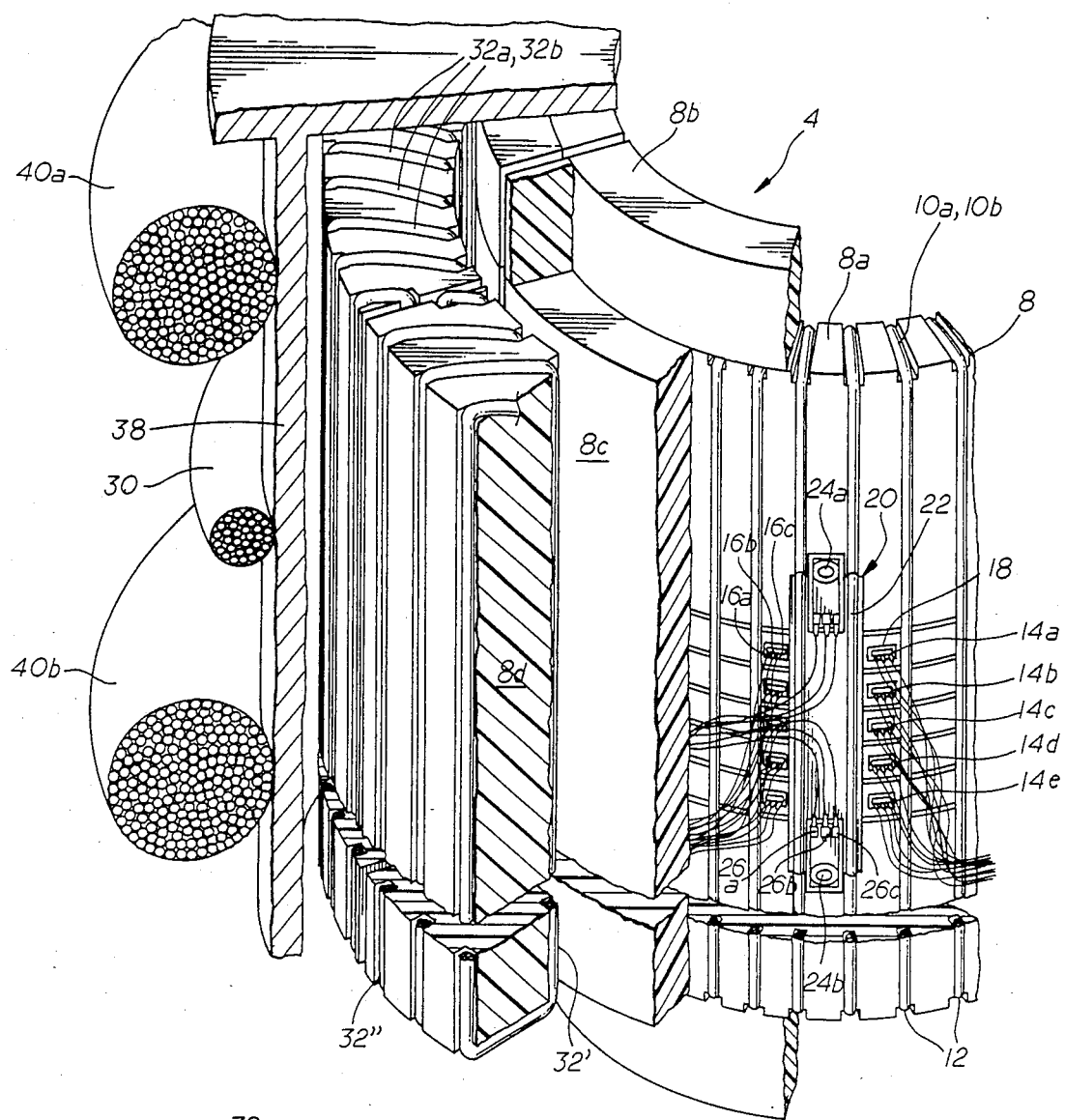
FIG. 2 is a view of a segment of the tubing trip tool in the expanded configuration.
Figure 3:
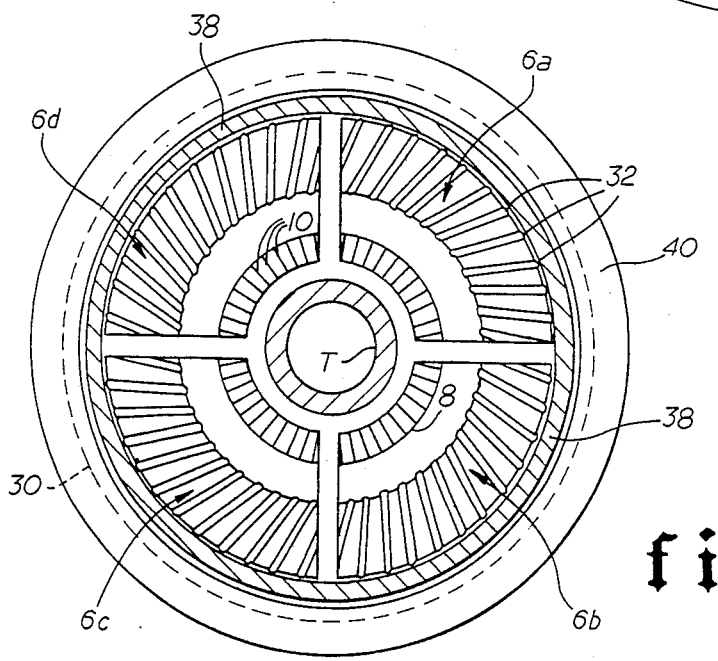
FIG. 3 is a view of a section of the tubing trip tool head in the expanded configuration.
Figure 4:
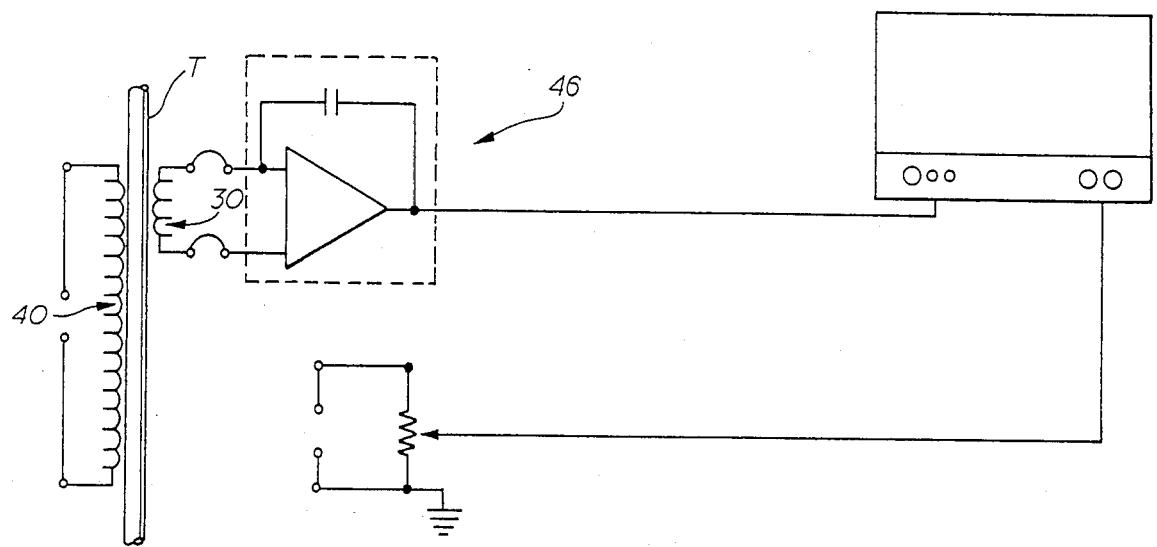
FIG. 4 is a view showing the wall thickness measurement circuitry.

A segment of the tubing trip tool head 4 is shown in FIG. 2. The head includes two separate driving coils, two separate detecting coils, and a plurality of discrete detecting elements to determine the extent of defects in the tubing sections. A velocity detector for determining relative velocity between the head and tubing sections is also included. The preferred embodiment of this invention comprises an expandable head having four segments 6a-6d as seen in FIG. 3. Each segment is an encasement 8 which comprises multiple components. The encasement 8 is fabricated from a material that has the properties of an electrical insulator. In the preferred embodiment of this invention, encasement 8 can be formed from an encapsulation material or potting compound which will insure that the proper amount of space is maintained between the electrical components. The encapsulation material will occupy any spaces or voids surrounding the components, and will provide a barrier between the electrical components and the atmosphere surrounding encasement 8, thereby rendering encasement 8 safe for use on the wellhead where explosive vapors can be encountered.

Two separate AC detecting coils 10a and 10b are carried on the innermost insulating body section 8a. The circumferentially continuous coils 10a and 10b are wound in appropriate grooves on body section 8a and a plurality of separate loops are formed around body 8a. These separate loops, each of which contains conductors forming the separate detecting coils 10a and 10b, are positioned in a radial plane on encapsulating member 8a. Each loop is generally defined by two radially spaced, axially extending coil conductor sections and two axially spaced, radially extending coil conductor sections. The coil conductors then define an annular volume encircling the tubular sections passing axially therethrough. Radially extending planes between the coil conductors will be generally perpendicular to magnetic field lines detected by coils 10a and 10b as will be subsequently more completely discussed.

A plurality of flux leakage detecting elements 14a-14e are also located in the inner encapsulating body section 8a. In the preferred embodiment of this invention, each of the flux leakage detecting probes 14a-14e comprises a separate probe in which voltage is generated in response to the Hall effect. The plane of each Hall probe is perpendicular to the axis of the tubing trip tool head 4 and is located perpendicular to each tubular element moving axially relative to the tubing trip tool head 4. In the preferred embodiment of this invention, separate groupings of five Hall effect flux leakage detecting probes are positioned at different angular positions around the tubing trip tool head 4. Each of the Hall probes 14a–14e is received within corresponding slots 18 extending into the insulating body section 8a. In the preferred embodiment of this invention, five equally spaced probes are positioned at each angular location.

One or more velocity detectors 20 is positioned on the exterior of insulating body section 8a. In the preferred embodiment of this invention, each velocity detector 20 comprises a detector circuit or coil 22 having two or more Hall probes 24a and 24b located within the circuit. The plane of the velocity detector circuit or coil 22 is perpendicular to a radial plane extending through the tubing trip tool head 8. The plane of the individual Hall probes 24a and 24b in the velocity detector is perpendicular to the plane of the Hall probe 14a–14e used for flux leakage detection.

The AC magnetic detecting coils 10a and 10b, the flux leakage detecting probes 14a–14e and the velocity detector 20 are each radially spaced from the tubing element T in which defects are to be measured. In the segmented embodiment of the invention shown in FIG. 2, the individual segments can be shifted radially from a measuring position to an outer position to permit obstructions to move past the tubing trip tool head. Each of the detector coils is, however, spaced from the surface of the tubing T in the inner measuring position. In the preferred embodiment of this invention, the inner surface of the tubing trip tool head 4 is positioned approximately two-thirds of an inch from the surface of the tubing element T.

Insulated body sections 8b and 8c surround the detecting coils and probes mounted on insulating body section 8a. Epoxy or some other potting material can also be used to insure that all potentional electrical leakage paths are appropriately isolated from each other and from the atmosphere.

Outer AC driving coils 32a and 32b are positioned around insulating body section 8d. The AC drive coils 32a and 32b each comprise continuous coils having an angular conductor distribution similar to that of AC detecting coils 10a and 10b. The sinusoidal distribution in the coils 32a and 32b is relatively offset so that the conductor distribution phase differs between drive coils 32a and 32b. In the preferred embodiment of this invention, the conductor distribution is offset by 90° so that coil 32a can be referred to as a sine coil and coil 32b can be referred to as a cosine coil. Coils 32a and 32b each completely encircle the tubing trip tool head 4 and tubular element T with separate loops, containing conductors from each coil 32a and 32b, being formed in radial planes around the tubing trip tool head 4. On the exterior, AC driving coils 32 are encapsulated within the common encapsulating insulating body 8 of the tubing trip tool 2.

In the preferred embodiment of this invention, an outer metal sheath 38 can be positioned around the exterior tubing trip tool head. This outer metal sheath, which can be fabricated from a nonferromagnetic material, such as aluminum, serves as a carrier for the outer DC drive coils 40a and 40b. In the preferred embodiment of this invention, the DC drive coils are separated into two separate bundles. A single drive coil bundle can also be used. The encircling drive coils 40 contain a sufficient number of amp turns to saturate the tubular element T passing through the tubing trip tool. Encircling coil 30 extends completely around the circumference of the tubing trip tool head 4 and surrounds the tubular element T at a greater radial spacing than the detecting elements 10a and 10b, 14a–14e, and 20.

WALL THICKNESS MEASUREMENT

The tubing trip tool 2 measures the wall thickness of a tubing section by using a technique in which the total flux induced in the tubing section by a saturating magnetic field is measured. The ferromagnetic tubing section within the saturating magnetic field is saturated when the magnitude of the magnetic field induced in the ferromagnetic element is at a maximum and does not increase as a result of a further increase in the saturating magnetizing field. Thus the saturating magnetizing field can produce a uniform saturated magnetic field in a tubing section having a specified cross-sectional area. In other words, the total magnetic flux is dependent upon the cross-sectional area or wall thickness of the tubular section. If the saturating magnetizing field is uniform, the contribution of the total flux induced by the magnetization of the pipe material within a given area varies as the cross-sectional area of the tubing section. By providing a large number of amp turns in a coil 40 encircling a tubing section, a saturated magnetic field extending longitudinally within the wall of the tubing section can be produced.

The total flux through an area intersecting the axis of the tubing section and intersecting the longitudinal saturated magnetic field can be measured by pickup coil 30 encircling the tubular section. The area of the pickup coil would preferably, but not necessarily, be perpendicular to the axis of the tubing section. The total flux through the pickup coil can be detected by signal integration. The EMF induced in a pickup coil is directly related to the time rate of change of the flux through the coil. Thus the total flux can be detected by integrating the EMF produced in the coil over time. In fact, a virtually linear dependence of the total flux through the pickup coil with average wall thickness can be obtained. Thus a convenient direct measurement of average wall thickness can be made.

In the tubing trip tool 2, the saturating magnetizing field is applied by one or more DC drive coils 40. In the preferred embodiment of this invention, two drive coils 40a and 40b are positioned on the exterior of the tubing trip tool head 4 (see FIG. 2). The pickup coil 30 encircling the tubular section T detects the total flux, and the output of pickup coil 30 can be attached to a conventional integrator 46. The output voltage of the integrator is a direct measure of tubing wall thickness. If the tubing moves axially relative to the stationary saturating magnetizing field, a continuous measurement of total flux will result in a measurement of the wall thickness along the length of the tubing section. Conventional signal processing means can be used for comparing and correlating detected signals with average wall thickness.

This noncontact measurement of average wall thickness can be incorporated into the tubing trip tool 2 comprising the preferred embodiment of this invention. A sufficiently strong and uniform DC magnetizing field can be produced by a sufficient number of amp turns in coils 40a and 40b. For example, approximately 5,000 amp turns can saturate a 2⅜" OD pipe, a standard size tubing section used in an oil and gas well. In the preferred embodiment of this invention, a sufficient uniform longitudinal saturated magnetic field is produced in a tubing section moving relative to the saturating magnetic field within a range of velocities normally encountered in the removal of a tubing string from an oil or gas well. A coil having an overall height of less than one foot has been found to satisfactorily produce a longitudinal saturated DC magnetic field in the tubing section and an accurate measurement can be obtained of the average wall thickness.

LOCAL DEFECT DETECTION

The average wall thickness of a ferromagnetic tubular member or pipe can be determined by detecting the total flux induced by the saturating magnetizing field within the element. Qualitative information as to the changes in surface texture due to such factors as internal and external corrosion, can be determined by comparing average wall thickness at different locations on the tubular member. The difference between the signals produced in separate coils will not yield quantitative information as to the state of local defects in the tubular members.

In tubular sections used in oil and gas wells, corrosion on the tubular member can result in localized corrosion pits $D_1$ which can seriously reduce the strength of individual tubing sections. Since the thickness of the remaining wall of the tubular sections determines the ability of individual tubular sections to function in the work environment, the depth of local corrosion pits must be quantified to determine the acceptability of the tubular sections.

It is common practice to grade used tubing based upon the depth of corrosion pits. Although each separate corrosion pit would constitute a local defect $D1$, the dimensions of which would generally be less than the diameter of the tubular element, the nature of the corrosion phenomenon would result in a plurality of irregular and overlapping corrosion pits being located in the same general region on the interior of a tubular section. Of course the flux leakage will be dependent upon the overall size of individual corrosion pits and not just the depth of the corrosion pits. Thus the length and width of the corrosion pits would affect the flux leakage detected. Other factors, such as the contour or shape of the corrosion pits and the extent of any discontinuities in the shape of corrosion pits, would also affect the flux leakage. Thus the leakage fields of different pits having the same depth in a tubular section will differ for different lengths and widths of the pits as well as for a different contour of the pits. Background fields or noise due to unrelated phenomenon can also affect the signal corresponding to flux leakage and the saturated magnetic field within the pipe.

In the preferred embodiment of this invention, a plurality of flux leakage detecting elements 14 are disposed within the saturating magnetizing field. These flux leakage detecting elements are disposed at a plurality of axially spaced positions within the saturating magnetizing field. In the preferred embodiment of this invention, a plurality of discrete probes having an output produced by the Hall effect are used. In the preferred embodiment of this invention, identical flux leakage detecting Hall probes 14a–14e are equally spaced at five separate axial positions. Although only two sets of flux leakage detecting Hall probes 14a–14e are shown in FIG. 2, it should be understood that corresponding sets of multiple elements are circumferentially disposed around the tubing trip tool head to provide complete coverage arond the periphery of the tubular element to detect local defects, such as corrosion pits located at different angular positions.

In the preferred embodiment of this invention, the individual flux leakage detecting Hall probes are oriented such that the plane of the Hall sensing element is perpendicular to the axis of the moving tubular element. Hall elements, such as the type used herein, produce an output voltage proportional to the product of the input current, the magnetic flux density, and the sine of the angle between the magnetic flux density and the plane of the Hall generator. Thus a maximum voltage output from a given leakage field would be produced by orienting the individual flux leakage detecting Hall probes perpendicular to the saturated magnetic field. The DC drive coils 40a and 40b are positioned to induce a longitudinal or axial saturated magnetic field within the tubular element T. By orienting the probes 14a-14e perpendicular to the longitudinal saturated magnetic field within the pipe, the flux leakage detecting probes are situated to detect longitudinal changes in the magnetic field. Of course transverse magnetic field changes would also occur as a result inthe change in the longitudinal saturated field within the tubular member. Orientation of flux leakage detecting Hall probes perpendicular to the radius of a moving tubular section would be ideal to detect these transverse field changes. However, it is understood by those skilled in the art that the transverse magnetic field changes are related to longitudinal magnetic field changes. Thus a plurality of individual flux leakage detecting Hall probes oriented at right angles to the probes 14a–14e used in the preferred embodiment of this invention could also be used. Of course flux leakage detecting elements other than Hall probes can also be employed in the measurement of localized defects, such as the depth of corrosion pits. For example, the change in flux linking a coil will also result in a signal which can be employed for local defect measurement. However, the output signal from a coil must be integrated to obtain the same output independent of the velocity of the tubing element T, as would be obtained with a Hall probe.

It has been found that the magnitude of the flux leakage detected by elements 14 does not provide an adequate quantitative measure of the depth of local defects, such as corrosion pitting defects, on a tubular element. The fact that flux leakage is dependent upon the size and shape of localized defects, such as corrosion pitting, rather than upon the depth alone, is believed to account for the inability to measure localized defect depth by measuring flux leakage magnitude alone. However, it has been found if effects due to the length and width of defects, such as corrosion pitting, can be removed, the resulting signal results in an accurate measurement of the depth of the local defect.

In the preferred embodiment of this invention, a signal corresponding to the depth of local defects, such as defects due to corrosion pitting, can be determined by differentiation of the magnitude of the flux leakage relative to the axial or longitudinal dimension of the moving tubular member. A signal corresponding to the depth of local defects, such as defects due to corrosion pitting, can be obtained by comparing two derivatives of different orders, each with respect to the axial dimension of the flux leakage, obtained when the saturated magnetic fields at the maximum value of the flux leakage corresponding to each measured discontinuity. In the preferred embodiment of this invention, the second and fourth derivatives, determined by using finite element approximations, can be combined to produce a signal measuring the depth of the local defect. It has been found that the depth of a local defect can be measured in the following fashion.

$$d = k(f'')^a/(f'''')^b;$$

where
- d is equal to the depth of local defects, such as a defect due to corrosion pitting.
- k is an empirically determined proportionality constant.
- f'' is the second derivative of the flux leakage with respect to the axial or longitudinal dimension.
- f'''' is the fourth derivative of the flux leakage with respect to the axial dimension.
- a is an empirically determined factor.
- b is an empirically determined factor.

Of course other similar empirically determined relationships between the two non-zero derivatives might be used by those skilled in the art to obtain local defect depth without departing from the spirit of this invention. For the relationship employed herein, care must be taken that non-zero derivatives be used to avoid dividing by zero. The derivatives employed herein are being evaluated at their maximum where they are inherently non-zero.

Figure 5:
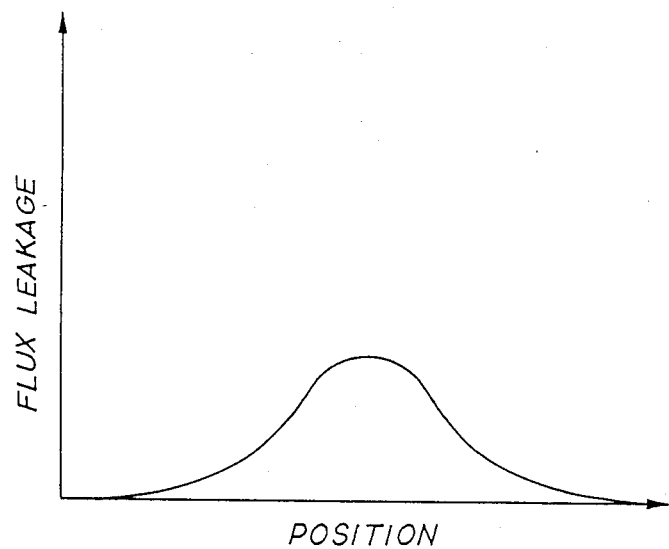
FIG. 5 shows the effect of movement of the tubular element upon flux leakage.
Figure 8:
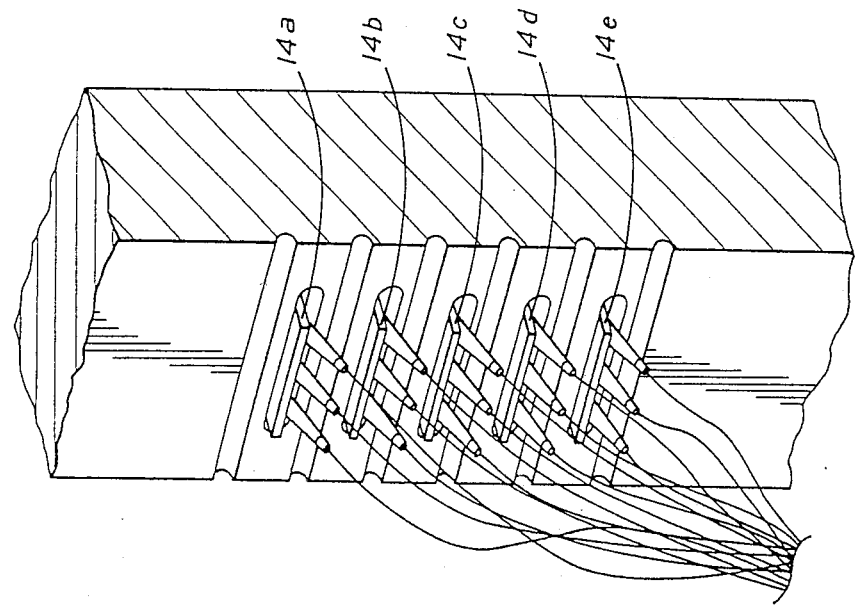
FIG. 8 is a view of Hall effect probes for measuring local defects.
Figure 7:
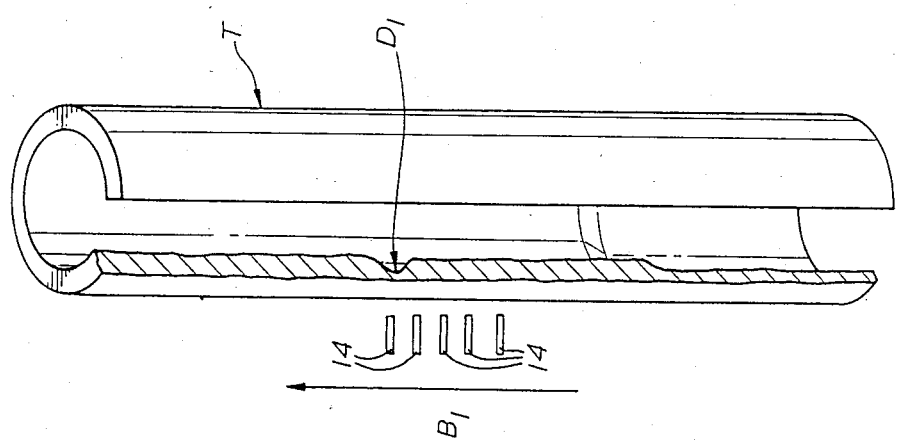
FIG. 7 is a view similar to FIG. 6 showing relative movement of the tubing.
Figure 6:
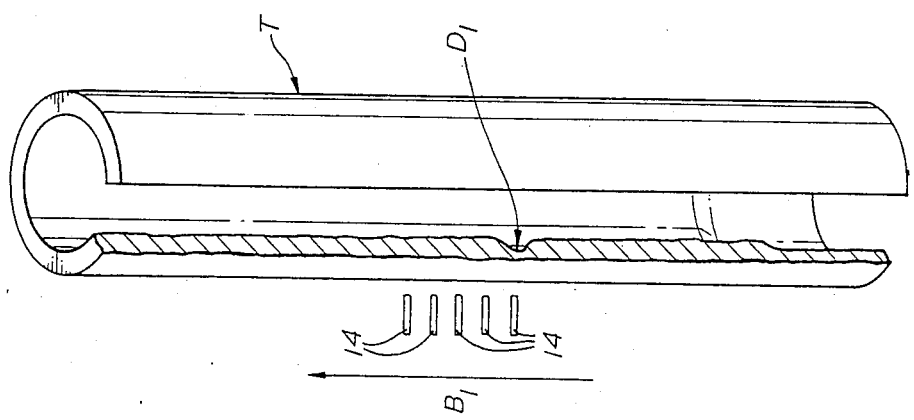
FIG. 6 is a view showing the tubing string and the detectors for measuring local defects.
Figure 10:
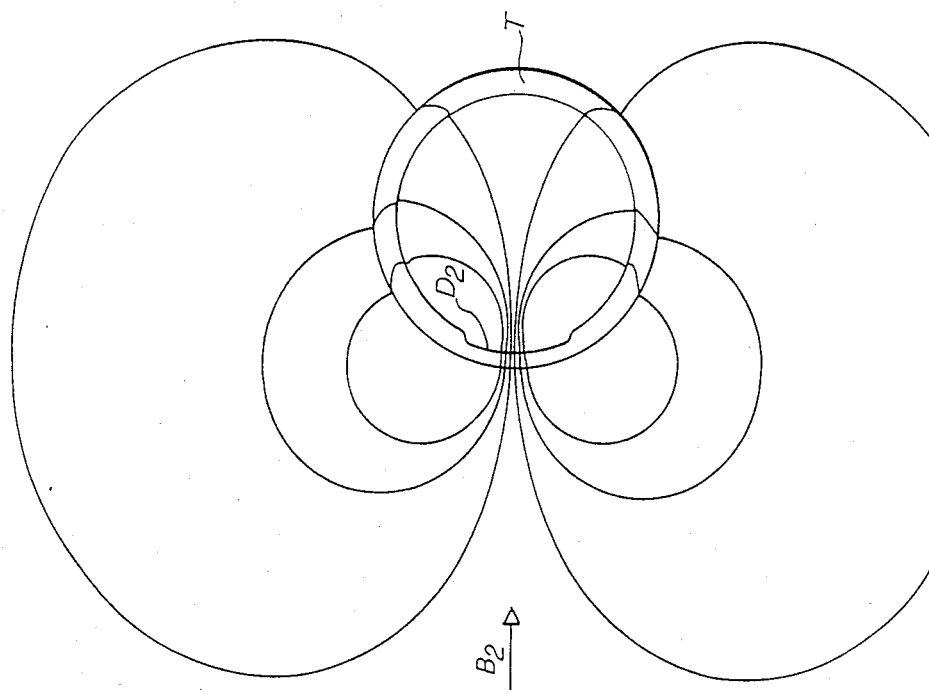
FIGS. 9-11 illustrate the effect of a rotating defect in a tubular member on magnetic field lines due to relative rotation between the driving magnetic field and the tubular member, the field lines shown corresponding to the difference between the total magnetic field lines in a tubular member with no detectable defects and a corresponding tubular member with the defect as shown.
Figure 9:
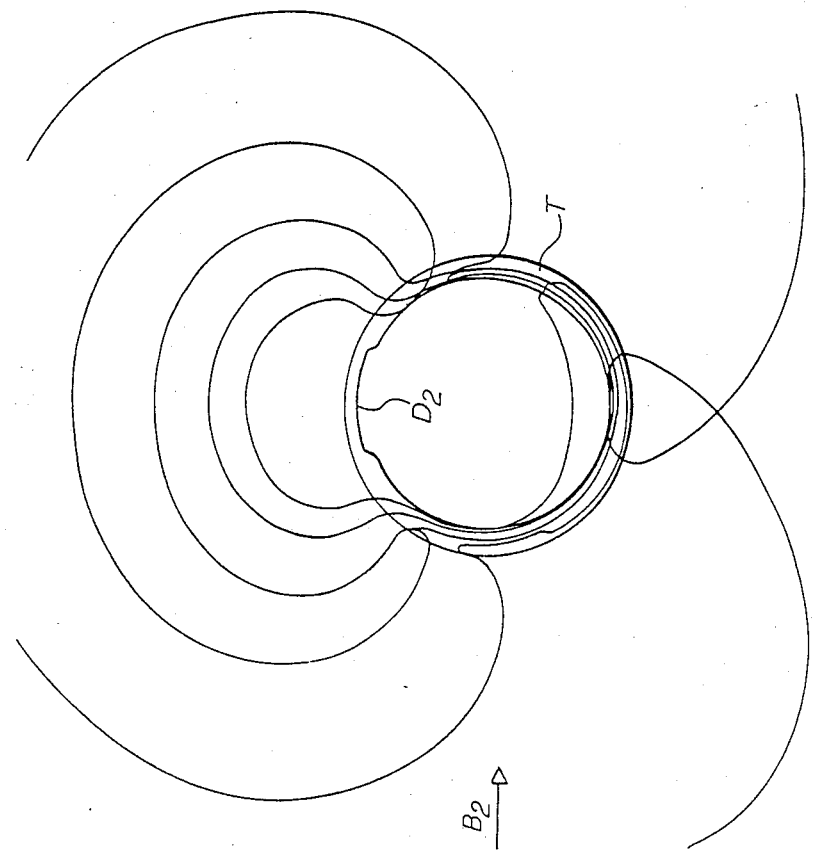
Figure 11:
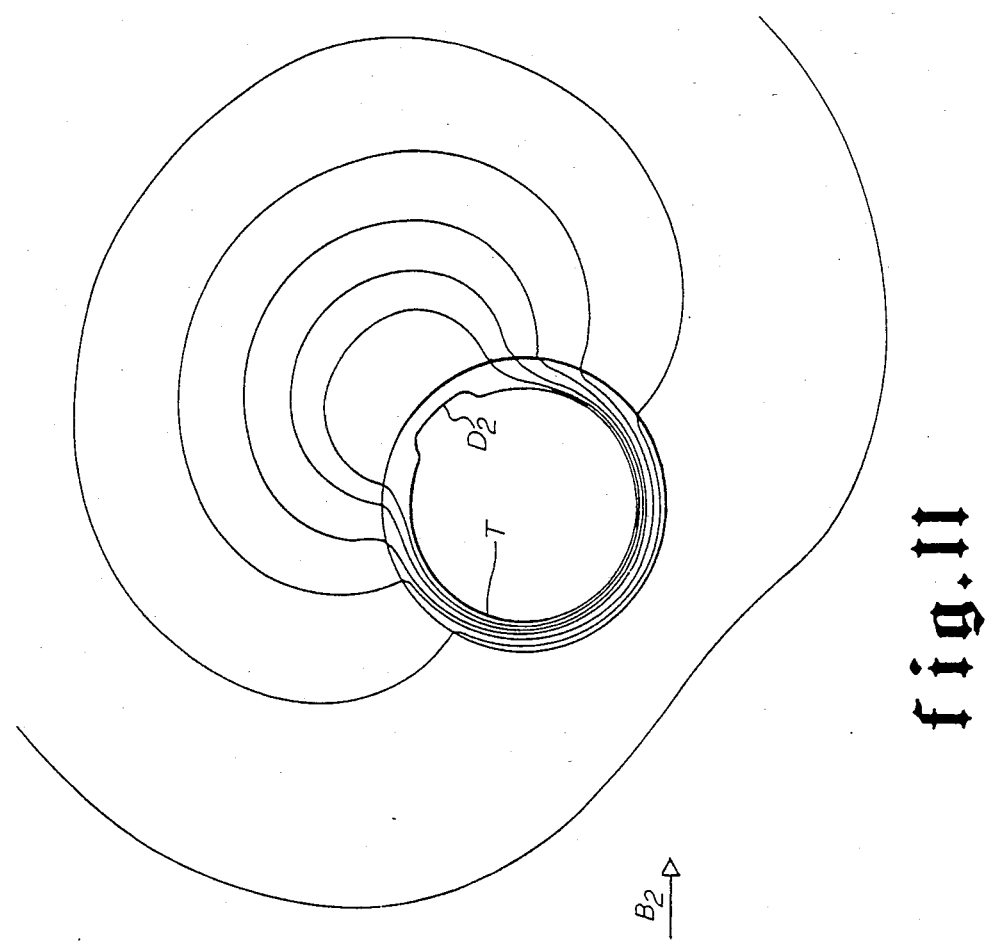

In the preferred embodiment of this invention, the geometric filtering or numerical differentiation is obtained by using a plurality of axially evenly spaced flux leakage detecting elements 14a-14e which remain fixed relative to each other (See FIGS. 6 and 7). By multiplying the magnitude of the flux leakage simultaneously detected in each element by appropriate factors and summing, the value of each of the higher order derivatives can be determined. In the preferred embodiment of this invention, the factors used to multiply the output of individual flux leakage detecting elements are constants and are chosen such that the value of each of the derivatives will be zero if the flux leakage is unchanging. The conventional voltage generating flux leakage detection elements 14a-14e employed in the preferred embodiment of this invention are spaced apart and a simultaneous value of flux leakage is obtained from each flux leakage detecting element 14. By detecting the value of flux leakage on opposite sides of the center, the value of the derivative in question may be obtained at the center location. Thus when the flux leakage reaches a maximum at the center of the detector array, the derivative of the appropriate order at the maximum flux leakage will be determined. This detector array will also evaluate the shape of the leakage field in the vicinity of the maximum flux leakage (see FIG. 5). By comparing non-zero derivatives of the flux leakage of different orders, the unchanging DC fields and that background noise which is basically unchanging with respect to the fluctuation of the flux leakage in the vicinity of a local defect will be reduced. Comparison of the non-zero derivatives will thus yield information as to the change in the saturated magnetic field due to flux leakage and will also give information on the shape and extent of the corrosion pitting field, from which information as to the length and width of the local defect, such as the length and width of a corrosion pit, will be eliminated. Thus the signal obtained from the differentiation and the comparison of different order derivatives will yield the signal which is proportional to the depth of a local defect.

It should be understood that similar information could be obtained by employing a single flux leakage detecting element and determining the magnitude of the flux leakage at each of the positions corresponding to the multiple elements 14a-14e used in the preferred embodiment of this invention. However, the use of a single element to measure the flux leakage at separate positions would require an accurate determination of the exact position at which the multiple measurements were taken. For a detecting apparatus used to measure local defects in a tubular element which is not moving at constant speed, such a position indication would require an accurate measure of the velocity and hence position of the tubing element relative to the saturating magnetizing field. By using a plurality of elements rather than an individual detecting element, no velocity measurement is necessary for the measurement of critical parameters of local defects, such as the depth of a localized corrosion pitting defect.

The signals generated by the flux leakage field can be processed in a conventional manner to calculate the depth according to the generalized numerical derivative function presented herein or according to other algorithms measuring an appropriate variation of depth of a localized defect to the flux leakage obtained by numerical differential or by other geometric filtering means. Such signal processing can be performed by conventional analog or digital means such as comparator C shown in FIG. 1 for comparing and correlating signals to local defect depth, and appropriate signal processing circuitry can be incorporated to compensate for variations in the separate flux leakage detecting elements due to such factors as varying temperature sensitivities.

AXIAL DEFECT MEASUREMENT

The bore of a tubular member or tubing section T used in a tubular string in a subterranean oil and gas well can often have axially extending defects $D_2$ located at one or more circumferential positions on the tubing. An example of axially extending defects are defects due to sucker rod wear. Sucker rod wear on the bore of the tubing occurs when the sucker rod contacts the tubing during reciprocal movement of the sucker rod. However, sucker rod interference is not uniform around the circumference of the bore of the tubing section or tubular element. Sucker rod wear often occurs at only one circumferential location, although it is not uncommon for a sucker rod to oscillate laterally causing sucker rod interference at two opposite points. The loads placed on the individual sucker rod assembly will normally result in continual interference between the sucker rod and the tubing at the same locations.

Since the length of the sucker rod stroke is normally large compared to the diameter of the tubing, the length of the sucker rod defects can be expected to be greater than the diameter of the tubing. Although sucker rod wear is a common occurrence, points at which the sucker rod interferes with the bore of a tubing string may occur in only a fraction of the tubing sections if the distance between interferring sucker rod nodes is greater than the length of individual tubing sections. Not only must the tubing sections subjected to sucker rod wear be identified, but the depth of axial defects, such as sucker rod wear defects, must also be measured. The depth of the defects due to sucker rod wear is significant because the reduction in the strength of the individual tubing section increases with the depth of the axially extending sucker rod wear defect.

Axial defects $D_2$, such as defects due to sucker rod interference, can be detected by employing a fluctuating AC magnetizing field $B_2$ in addition to a uniform DC magnetizing field $B_1$. Even if a uniform DC magnetizing field in the longitudinal or axial direction is of sufficient intensity to saturate the ferromagnetic element or tubular section within the DC field, as is the case with the field used to determine wall thickness, the addition of a fluctuating AC transverse magnetic field will result in detectable changes in the magnetic state of the ferromagnetic element located within both fields. In fact, the DC field enhances the penetration of the AC field in the tubular sections. Of course the detectable changes resulting from the addition of the fluctuating transverse field will be dependent upon the geometry of the tubular element. For example, the response of an undamaged tubing section would differ from the response of a similar tubing section containing an axially extending defect, such as a rod wear interference defect. In the preferred embodiment of this invention, the changes due to such axially extending defects as sucker rod interference defects $D_2$ in an oil field tubular section can be detected even where the strength of the fluctuating transverse magnetic field is significantly less than the strength of a uniform saturating DC magnetizing field. It has been found that measurement of axial defects, such as sucker rod interference defects, can be made by applying a sinusoidal transverse magnetizing field having a frequency of approximately 100 Hz. and an intensity of approximately 1/10th the intensity of a uniform saturating magnetizing field applied in the longitudinal direction. In the preferred embodiment of this invention, drive coils 32 are used to apply such a fluctuating magnetizing field.

In order to obtain full circumferential coverage of a tubular section and to obtain a measurable response, the preferred embodiment of this invention comprises an apparatus and method for rotating the fluctuating AC magnetizing field around the tubular section T as the tubing section moves axially relative to both the AC magnetizing field $B_2$ and the uniform DC saturating magnetizing field $B_1$. Thus the rod wear defect response measured in the preferred embodiment of this invention is due to an AC magnetizing field rotating around the tubing section and having a constant magnitude.

VELOCITY AND POSITION DETECTOR

Figure 12:
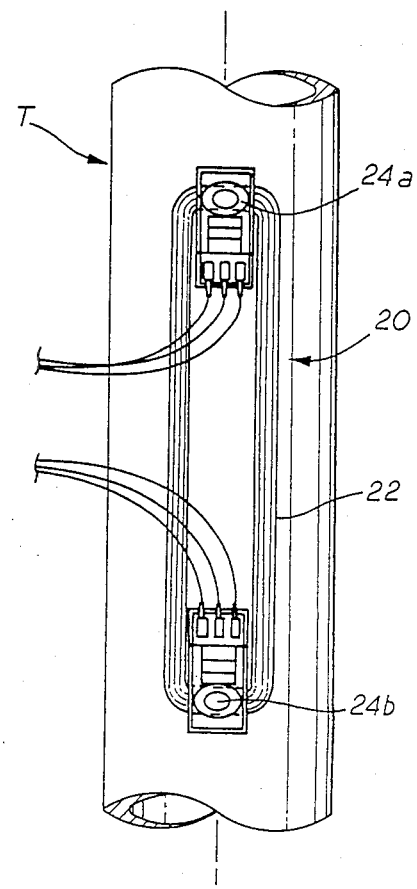
FIG. 12 is a view of a velocity detector mountable on the tubing trip tool head.

The cross-sectional area of a moving tubular element, the depth of local defects, such as corrosion pitting defects, and the size of longitudinally extending defects, such as defects due to sucker rod interference, can be determined by detector 4 independent of the velocity of the tubular element T relative to the detector. There may also be a need to determine the velocity of the tubular element T relative to the tubing trip tool 2. For example, it may be necessary to not only determine the existence and size of a defect in a particular tubing section of tubular string T, but it may be necessary to determine the position of the defect in both the tubing string and in the constituent tubular section. A noncontact velocity detector 20 is shown positioned on the tubing trip tool head 4 in FIG. 2. The preferred embodiment of each velocity detector used in this invention comprises two detector elements 24a and 24b in which a signal is produced by the magnetic field. In the preferred embodiment of this invention, detector elements 24a and 24b comprise elements in which the voltage is generated due to the Hall effect. These Hall probes 24a and 24b are then incorporated into a velocity detector coil 22 as shown schematically in FIG. 12. The signal produced in the coil is related to both the velocity and the magnetic field sensed by the coil. The signal in the coil is proportional to the vector cross product of the velocity and the magnetic field whereas the signals in the Hall probes are due solely to the magnetic field. The output voltage of a pickup coil near a changing magnetic field is proportional to the rate of change of the field of fixed spatial orientation passing by the coil, then any output voltage is proportional to the product of the field strength and the field velocity.

The changing magnetic fields due to the velocity of the tubular element T are the magnetic leakage fields emanating from the pipe either as pitting signals, as signals due to average wall changes, or as pipe noise. For example, a leakage field is created by permeability fluctuations within the ferromagnetic tubular element T. In the preferred embodiment of each velocity detector, the two Hall probes 24a and 24b are incorporated into the coil 22 with the Hall probes oriented to detect radial changes in the leakage fields. When the coil and Hall probes are oriented as shown in FIG. 2, the coil voltage is equal to the product of the number of turns in the coil, the velocity of the tubular element, the width of the coil, and the difference between the radial components of the magnetic leakage field at the two ends of the coil. The voltage of each Hall probe is equal to the gain of the Hall probe device times the radial component of the leakage field of the Hall probe. The ratio of the coil voltage to the difference in the voltage between the two Hall probes thus determines the pipe velocity.

END COUPLING DETECTOR

The noncontact velocity detector described herein can be used to determine the axial position of a defect in an inspected tubular member. Knowledge of the defect location in specific tubular sections forming the tubing string is important, and knowledge of the defect location in the tubing string is also significant in that such knowledge would permit the operator to determine the exact location in the well at which wall thickness reduction, corrosion pitting or wear due to sucker rod interference is a problem. Such knowledge would permit construction of a string profile to determine significant problem areas.

In order to construct a string profile and to accurately obtain information as to the location of defects in any particular tubular string, the position of the tubing string relative to the well head must be determined. In the preferred embodiment of this invention, the location of the tubing string is determined by use of the noncontact velocity detector and by use of a noncontact end coupling detector. For conventional tubular strings, such as casing, production tubing and completion strings used in oil and gas wells, the individual sections are joined by end couplings.

There are two common types of end couplings. The first consists of a collar having internal threads on both ends which is used to join two lengths of casing, tubing or conduit. The cross-sectional area of the separate coupling member and the end portions of the tubing sections engaging the separate member will be greater than the cross-sectional area of the tubular section intermediate its ends. A second type of end coupling comprises an upset section on the ends of adjacent tubing sections. The ends of adjacent tubing sections have mating threads in the vicinity of the upset ends, and the tubular sections are joined directly without the necessity of employing a separate coupling section or collar. These directly engagable tubular sections are, however, upset, with the portion of the tubing section in which threads are machined being thicker than the remaining portion of the tubing section. Thus the cross-sectional area in the vicinity of the end coupling is greater than the cross-sectional area of the tubing intermediate its ends whether a separate collar is used or whether interengagable mating threads are employed on adjacent tubular sections.

Figure 13:
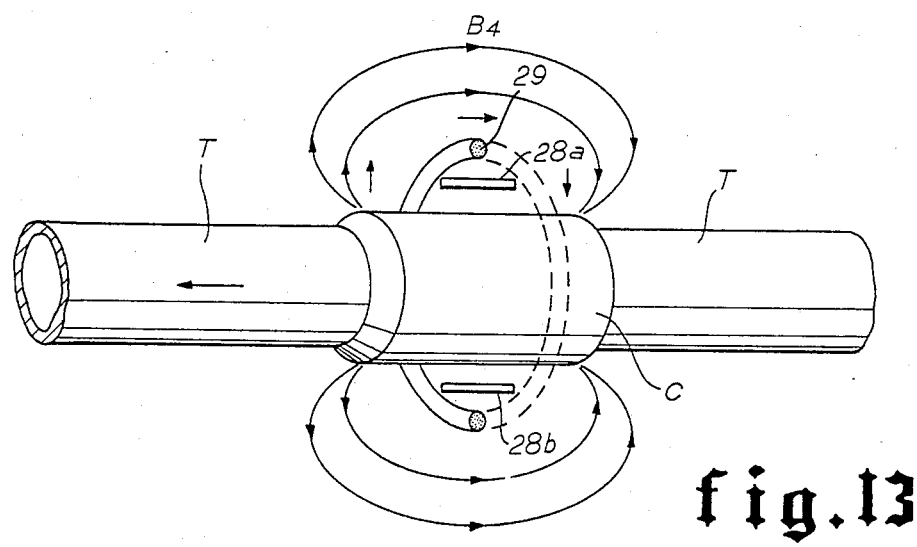
FIG. 13 is a schematic of the end coupling detector.

The exact location of each tubing section, and thus the location within the tubular string can be determined by detecting both the presence and the direction of movement of each end coupling. In the preferred embodiment of this invention, a magnetic field having a uniform strength and fixed relative to the well head is applied to the portion of the tubular string and tubular sections in the vicinity of the well head. An induced magnetic field in the tubular section results. FIG. 13 shows tubing sections T interconnected by end coupling C and the lines of magnetic flux representing the induced magnetic field B4 in the area of end coupling C. Since the cross-sectional area at end coupling C is greater than the cross-sectional area of tubing T, the strength of the magnetic field B4 in the vicinity of the end coupling will be greater than the strength of the magnetic field induced in the tubular section intermediate its ends. If the strength of the magnetic field B4 detected at the well head is greater than a predetermined reference value in excess of the field strength normally induced in a tubing section having a constant cross-sectional area intermediate its ends, the presence of a coupling can be distinguished from normal variations in the strength of the induced magnetic field in the tubing section. In the preferred embodiment of this invention, the strength of the reference signal or the threshold value of the magnitude of the induced magnetic field would be less than the magnitude of a magnetic field normally induced by an end coupling of known dimensions to account for slight variations of the magnetic field induced in the coupling.

In normal drilling, production and completion operations, the tubular sections comprising the tubular string are intermittently lowered and raised during either insertion or removal into or from the well. Therefore simple detection of the presence of an end coupling in the vicinity of the well head will not be sufficient to identify specific tubular sections comprising the tubular string or to identify the location of a tubular section within the tubular string. Therefore it will be necessary to identify the direction in which the coupling moves with relation to the well head. By identifying both the presence of the coupling at the well head and the direction of movement of the coupling with respect to the well head, each instance in which the coupling passes the well head in either direction can be stored in a conventional memory, and conventional computing means can be provided to tabulate the number and location of each end coupling encountered during insertion or removal of the tubular string into or from the well.

In the preferred embodiment of this invention, each end coupling, and its direction of movement are detected and counted by first magnetically detecting the presence of an end coupling having an enlarged cross-sectional area in the manner previously described. One or more detectors capable of generating signals of opposite signs corresponding to movement of the tubular strings T and end coupling C in opposite directions relative to the detector are employed to determine the direction of movement of an end coupling C. In the preferred embodiment of this invention, an encircling coil 29 similar to encircling pickup coil 30, which is used to determine the average wall thickness of the tubular section, is employed to detect an end coupling C having a greater thickness than the tubular section. Encircling coil 29 functions in the same manner as coil 30 as previously described with respect to measurement of the wall thickness. Indeed an apparatus in accordance with this invention could employ the same encircling coil, both for the wall thickness measurement of the tubular string T and to detect the presence of an enlarged end coupling C.

Once the presence of the end coupling has been detected by encircling coil 29, the direction of movement can be detected by separate detectors, such as detectors 28a and 28b. In the preferred embodiment of this invention, detectors 28a and 28b comprise Hall probes which generate a voltage proportional to the product of the input current, the magnetic flux density, and the sine of the angle between the magnetic flux density and the plane of the Hall generator. These elements are similar to the elements used for corrosion pitting detection and the voltage is produced in response to the electromagnetic phenomenon generally referred to as the Hall effect. The sign of the output voltage of Hall probes 28a and 28b will be opposite when subjected to magnetic lines of force in a magnetic field extending in opposite directions. As shown in FIG. 13, in which the direction of movement of the tubular string T is in the direction of the arrow, the magnetic lines of force of magnetic field 4 extend in the directions shown. Magnetic lines of force for the end coupling C increase in intensity as the end coupling C moves into an applied magnetic field when the magnetic lines of force extend outward as shown. At the trailing edge of the end coupling C, the magnetic lines of force in the induced magnetic field B4 extend inwardly toward the tubular string T and end coupling C as shown schematically in FIG. 13. Thus the Hall probes 28a and 28b will be subjected to magnetic lines of force or flux extending in opposite directions during passage of end coupling C through the applied magnetic field. When the Hall probes 28a and 28b are positioned near the leading edge of the moving end coupling C, the magnetic lines of force will extend radially outward. When the Hall probes 28a and 28b are adjacent the trailing edge of the end coupling C, they will be subjected to magnetic lines of forces extending inwardly toward end coupling C. Thus the voltage generated by Hall probes 28a and 28b in the vicinity of the leading edge of end coupling C will have the opposite sign from the voltage generated when the Hall probes 28a and 28b are in the vicinity of the trailing edge of end coupling C. One sequence of the signs of the voltage generated by Hall probes 28a and 28b will correspond to movement of the tubing string T and end coupling C in the direction shown in FIG. 13. Movement of the tubing string T and the end couping C in the opposite direction will result in an opposite sequence for the signs of the voltage generated by the Hall probes 28a and 28b. Thus the direction of movement of end coupling C through the applied magnetic field can be recognized by conventional computing means and specific tubular sections can be located.

When used in conjunction with a position indicator, such as would be provided by a device capable of measuring the velocity of the tubing string T, a profile of defects, including average wall thickness reduction, corrosion pitting, and wear due to sucker rod interference, can be tabulated as a function of the position of the tubular string in the well. Such information can give the operator valuable insights on the phenomenon being encountered within an subterranean oil or gas well. Furthermore, the use of the end coupling detector and the velocity detector described in the preferred embodiment of this invention will permit an accurate tabulation of defects in individual used tubing sections, to permit the operator to determine if such tubing sections should be replaced.

Although the invention has been described in terms of the specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A method of determining the extent of defects in a ferromagnetic element during axial movement of the ferromagnetic element, comprising the steps of:
   applying a saturating magnetic field to the ferromagnetic element of a sufficient intensity to produce a saturated magnetic field in the portion of the ferromagnetic element passing through the magnetizing field;
   positioning a plurality of axially spaced flux leakage detecting elements adjacent the ferromagnetic element to determine the shape and amplitude of flux leakage in the saturated magnetic field in the vicinity of the defects; and
   determining the depth of the defects by comparing two non-zero derivatives of different orders with respect to an axial component of the flux leakage in the saturated magnetic field as altered by the defects.

2. The method of claim 1 wherein the shape and amplitude of the flux leakage is obtained by combining signals from the plurality of flux leakage detecting elements disposed at positions fixed relative to the saturating magnetic field.

3. The method of claim 2 wherein the two non-zero derivatives are second and fourth derivatives of the flux leakage.

4. The method of claim 3 wherein the plurality of flux leakage detecting elements each provide a voltage output which increases monotonically with the flux leakage, and the voltage across each flux leakage detecting element is measured.

5. The method of claim 4 in which flux leakage detecting elements are disposed in surrounding relationship to the relatively moving ferromagnetic elements.

6. The method of claim 5 wherein the flux leakage detecting elements are located at positions in which the saturating magnetic field is constant.

7. The method of claim 1 in which the flux leakage detecting elements comprise voltage generating elements.

8. The method of claim 7 wherein the flux leakage detecting elements comprise elements in which a voltage is generated by Hall effect.

9. The method of claim 1 wherein the depth of multiple defects is determined without substantial influence by irregular lengths and widths of the multiple defects.

10. The method of claim 9 wherein the depth of local defects is determined by signal processing employing the plurality of detecting elements selectively spaced geometrically relative to the ferromagnetic element to measure the flux leakage.

11. The method of claim 1, wherein the derivatives of the axial component of the flux leakage in the saturated magnetic field are compared at a maximum value of the flux leakage.

12. A method of determining the extent of defects in a continuous ferromagnetic tubular string formed of a plurality of interconnected tubular elements, during axial movement of the tubular string, comprising the steps of:
   successively applying a saturating magnetic field to each tubular element of sufficient intensity to saturate the portion of the tubular element within the saturating magnetic field during movement of each tubular element therethrough;
   detecting a change in relative values of two non-zero derivatives of a different order of flux leakage in the saturated magnetic field to measure the depth of local defects in each tubular element by positioning a plurality of axially spaced flux leakage detecting elements adjacent the ferromagnetic tubular elements to determine the shape and amplitude of the flux leakage field in the vicinity of the defect.

13. The method of claim 12, wherein the depth of multiple defects is determined without substantial influence by irregular lengths and widths of the multiple defects.

14. The method of claim 12, wherein the depth of local defects is determined by signal processing employing the plurality of detecting elements selectively spaced geometrically relative to the ferromagnetic element to measure the flux leakage.

15. The method of claim 12 wherein the saturating magnetic field is a DC saturating magnetic field which induces a longitudinal saturated magnetic field into the tubular element.

16. The method of claim 15 wherein the plurality of flux leakage detecting elements are functionally responsive to an axial component of the flux leakage in the saturated magnetic field at a maximum value of the flux leakage to measure the depth of each local defect in each tubular element.

17. The method of claim 16 wherein the plurality of flux leakage detecting elements for detecting the depth of multiple local defects are substantially insensitive to varying lengths and widths of the multiple local defects.

18. In a method of determining the extent of defects in a ferromagnetic element during axial movement of the ferromagnetic element, in which a saturating magnetic field of a sufficient intensity to produce a saturated magnetic field is applied to a portion of the ferromagnetic element passing through the magnetic saturating field to detect cross-sectional area defects along the axis of the ferromagnetic element by detection of the total magnetic flux generated by the saturated magnetic field, and in which a fluctuating magnetic field in addition to the saturating magnetic field is applied to detect axially extending defects located at discrete lateral locations relative to the axis of the ferromagnetic element by detection of the driven fields induced in the ferromagnetic element by the fluctuating magnetic field;

a step of comparing two derivatives, each of a different order, of an axial component of the flux leakage in the saturated magnetic field as altered by the defects to measure the depth of defects in the ferromagnetic element by positioning a plurality of axially spaced flux leakage detecting elements adjacent the ferromagnetic element to determine the shape of the flux leakage field in the vicinity of the defect.

19. The method of claim 18, wherein the step of detecting flux leakage comprises detecting a change in flux leakage by combining signals from a plurality of flux leakage detecting elements.

20. The method of claim 19 wherein the depth of defects is determined by signal processing employing the plurality of flux leakage detecting elements selectively spaced geometrically relative to the ferromagnetic element at positions fixed relative to the saturating magnetic field.

21. A tool for determining at the wellhead the extent of defects in ferromagnetic tubing sections of a continuous tubing string used in a subterranean well bore as the tubing string travels into or out of the well bore, comprising:

means transversely spaced from the tubing string for successively applying a saturating magnetic field along the length of each tubing section of sufficient intensity to saturate the portion of the tubing section within the saturating magnetic field as the tubing string travels axially relative to the wellhead;

means transversely spaced from the tubing string for detecting flux leakage in the saturated magnetic field as altered by the defects of each tubing section; and means for correlating the flux leakage in the saturated magnetic field of each tubing section to the depth of corrosion defects on each tubing section, including means for comparing two non-zero derivatives of different orders of the flux leakage in the saturated magnetic field.

22. The tubing trip tool of claim 21 wherein the means for applying a saturating magnetic field comprises means for applying a DC magnetic field.

23. The tubing trip tool of claim 22 wherein the means for applying the saturating magnetic field comprises electric coil means encircling the tubing string at the wellhead.

24. The tool of claim 21 where the means for detecting flux leakage comprises means for detecting primarily a longitudinal component of the flux leakage in the saturated magnetic field.

25. The tool of claim 24 wherein the means for detecting the longitudinal component of the flux leakage comprise voltage generating elements.

26. The tool of claim 25 wherein the voltage generating elements comprise elements in which a voltage is generated by Hall effect and in which the voltage generating elements are oriented transversely to measure the longitudinal component of the flux leakage.

27. The tool of claim 24, wherein the means for detecting flux leakage detects a change in a maximum value of the flux leakage.

28. The tubing trip tool of claim 21 wherein the means for detecting flux leakage comprise a plurality of axially spaced elements in which the voltage is generated by Hall effect.

29. The tubing trip tool of claim 21 wherein the means for correlating the flux leakage in the saturated magnetic field to the depth of corrosion defects comprises means for correlating the individual depth of multiple corrosion defects having irregular lengths and widths.

30. The tool of claim 21 wherein the means for detecting flux leakage is insensitive to the axial velocity of the tubing string.

31. The tubing trip tool of claim 21 wherein the means for detecting flux leakage in the saturated magnetic field to the depth of corrosion defects comprises:

a plurality of voltage generating elements encircling the tubing string and axially spaced to determine the shape of the leakage field.

* * * * *